United States Patent [19]

Lewis

[11] 4,354,835
[45] Oct. 19, 1982

[54] SUPPORT FOR MOUNTING METAL MIRROR ON TEETH

[76] Inventor: Cheri J. Lewis, 240 S. La Cienega Blvd. #301, Beverly Hills, Calif. 90211

[21] Appl. No.: 253,796

[22] Filed: Apr. 13, 1981

[51] Int. Cl.³ .............................................. A61B 1/24
[52] U.S. Cl. ..................................................... 433/30
[58] Field of Search ........................................... 433/30

[56] References Cited

U.S. PATENT DOCUMENTS 1,397,090 11/1921 Dimas .................................... 433/30

Primary Examiner—Robert Peshock
Attorney, Agent, or Firm—Dominick Nardelli

[57] ABSTRACT

The support has an elongated body whereon at one end is swivel mounted a dental mirror and at the other end is disposed a spring clip means which is capable of engaging a tooth so that the mirror is independently supported within the mouth of the person wherein dental work is being performed.

4 Claims, 4 Drawing Figures

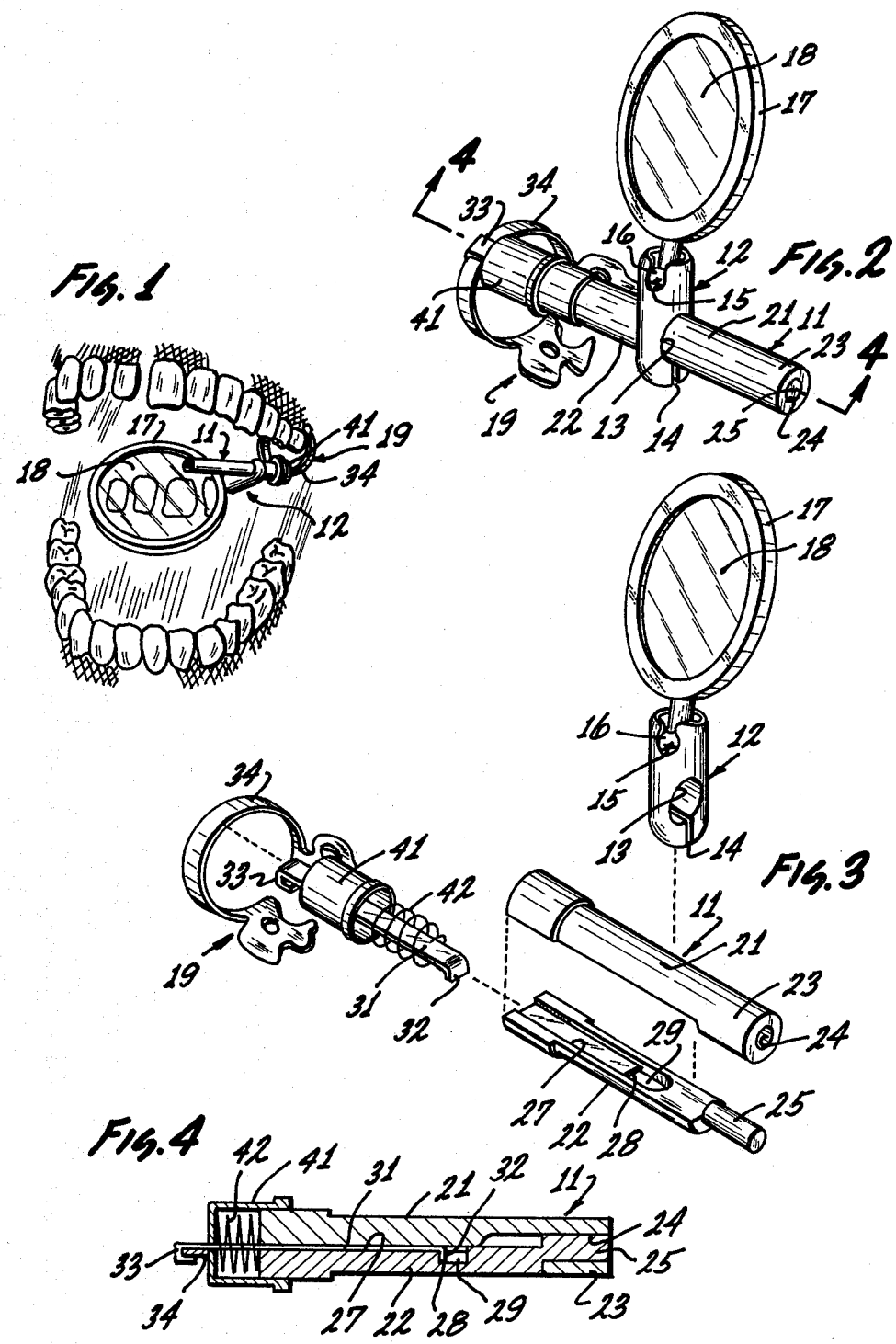

4,354,835

SUPPORT FOR MOUNTING METAL MIRROR ON TEETH

FIELD OF THE INVENTION

This invention relates to dental mirrors and more particularly to dental mirrors that have a means of support which mount onto a person having dental problems.

BACKGROUND OF THE INVENTION

Almost everyone has seen dental mirrors and knows something about their utility. One of the main functions of a dental mirror is to allow the dentist to view the commonly unseen sides of a persons teeth, which sides face the interior of the mouth. Up to now, dental mirrors consisted of a round spectral disk mounted at an angle at the end of a long slender rod. To use the mirror the dentist, depending on whether he was right or left handed, held a working tool, such as a drill in one hand, and the mirror in the other hand. Thus both hands were occupied, and if another tool is needed, obviously, the first tool had to be set down before the second tool could be picked up. One can see that the dentist was limited to using one tool at a time.

As the art of dentistry progressed, the dentist discovered that in some cases, he could perform a better job if he could use two working tools at the same time instead of having one hand tied to a dormant device such as the mirror, which is only an aid to the dentist in performing his duties. In such situations, some dentists summon an assistant to help them. However, this is undesirable, because too many hands would be located within the region of the mouth.

OBJECT OF THE INVENTION

An object of this invention is to provide a simple practical means for supporting a mirror as used in dentistry.

Another object of this invention is to provide a means which allows one to fixedly mount a dental mirror to one's teeth so that the mirror is disposed within the cavity of the mouth.

These and other objects and features of advantages will become more apparent after one studies the following description of the preferred embodiment of my invention together with the appended drawing.

BRIEF DESCRIPTION OF THE DRAWING

FIG. 1 is a schematic representation of a patient's open mouth wherein the mirror with the novel support means is placed.

FIG. 2 is an assembled pictorial view of the dental mirror with the support means removed from one's mouth.

FIG. 3 is an exploded pictorial view of the support means of FIG. 1 showing the individual parts.

FIG. 4 is a cross-section of the body of the support means taken on line 4—4 of FIG. 2.

DETAILED DESCRIPTION OF THE DRAWING

Referring to the drawing, and to FIG. 1 in particular, the novel support means has a cylindrical body 11 onto which is slideably mounted a link 12 through its aperture 13 (FIG. 3). A slot 14 is formed at one end of link 12 and extends to aperture 13 to provide a springing action between the body 11 and the link 12 so that friction is used to hold the two items in a fixed relationship. At the other end of link 12 is formed a standard socket 15 into which is disposed a ball 16 which in turn is made integral with a disk shaped mirror 17. The spectral surface 18 of the mirror 17 is recessed below an annular rim therearound. On one end of the body 11 is disposed a standard spring clip 19 which is of standard design and is used by a dentist to grip a tooth. The length of the body 11 is such that it is capable of being disposed within a patients open mouth while clip 19 is gripping a tooth as shown in FIG. 1.

One can see that when my novel support is disposed within a patients open mouth the mirror 17 can be moved to any position and it is fixed until again moved.

Referring to FIG. 3, there is shown the preferred embodiment of my invention unassembled. This construction is preferred because its support can be readily disassembled to be put into an autocave or a sterilizing unit so as to insure sterilization. The spring clip 19 which is of a standard design is shown removed from the remaining parts. The body 11 is made of several parts. Two of the parts 21 and 22 are substantially semi-cylindrical, except that one end of part 21 has a tubular section 23 with an axial bore 24. Then the other part 22 has at one end an axially disposed pin 25 which is made to fit freely into bore 24. Part 22 has an elongated recess 27 with a shoulder 28 so that a portion 29 is deeper than the remaining portion of recess 27. Within recess 27 will be disposed a hook means 31 when the unit is assembled as shown in FIG. 1. The hook means 31 has at its inner end a 90° short flange 32 which is capable of engaging the shoulder 28 at its outer end. The means 31 has a U-shaped hook 33 which is capable of engaging the bight portion 34 of the clip 19 as shown in FIG. 1. To hold the parts tightly together, there is provided a cup 41 which has an oblong aperture (not shown) at its bottom to conform to the shape of the means 31. The inside diameter of cup 41 is such that the body 11, when assembled freely slides therein. A compression spring 42 is disposed around means 31 between the cup 41 and part 21 so that when the unit is assembled, the cup 41 is urged against the clip 19 and the flange 32 is urged against the shoulder 28, as shown in FIG. 4.

Having described the preferred embodiment of my invention, one skilled in the art, after studying the description of my preferred embodiment, could devise other embodiments without departing from the spirit of my invention. Therefore, my invention is not limited to the disclosed embodiment, but includes all other embodiments falling within the scope of the appended claims.

I claim:

1. A support for a dental mirror comprising;
   a cylindrical body;
   a link slideably mounted on said body so that the link slides axially along and rotatably about said body;
   said link having a socket formed at one end;
   a disk-shaped mirror, having a radially protruding ball formed thereon;
   said ball being disposed within said socket to swivel in relationship thereon; and
   a spring clip capable of gripping a human tooth;
   spring means for releasably mounting said spring clip on one end of said body.

2. The support of claim 1 wherein said means for releasably mounting said spring clip comprises:
   a hook having a stem which has a smaller cross sectional area than the cross sectional area of said body and said hook is capable of releaseably engaging said spring clip:

a cup having an aperture is disposed around said body with said hook protruding through said aperture;

a compressing spring is disposed within said cup so that said spring urges said respective end of said body away from said aperture in said cup.

3. The support of claim 1 wherein said cylindrical body comprises:

a first semi-cylindrical part; and a second semi-cylindrical part;

said first part has an elongated recess extending from the end that said hook is disposed towards the other end of said body;

a shoulder is formed in said recess spaced from the ends of said first part;

a stem which has said hook integrally formed at one end thereof and has a flange integrally formed on the other end thereof;

said flange is capable of engaging said shoulder and preventing said stem from becoming disengaged from said cylindrical body whenever said two parts are assembled to form said body.

4. The support of claim 3 wherein said means for releasably mounting said spring clip comprises:

a hook having a stem which has a smaller cross sectional area than the cross sectional area of said body and said hook is capable of releaseably engaging said spring clip;

a cup having an aperture is disposed around said body with said hook protruding through said aperture;

a compressing spring is disposed within said cup so that said spring urges said respective end of said body away from said aperture in said cup.

* * * * *